(12) United States Patent
Sista et al.

(10) Patent No.: US 8,852,607 B2
(45) Date of Patent: *Oct. 7, 2014

(54) EXCIPIENTS FOR USE IN ADENO-ASSOCIATED VIRUS PHARMACEUTICAL FORMULATIONS, AND PHARMACEUTICAL FORMULATIONS MADE THEREWITH

(75) Inventors: Hema S. Sista, Cupertino, CA (US); Yero J. Espinoza, Alameda, CA (US)

(73) Assignee: Genzyme Corporation, Framingham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/506,638

(22) Filed: May 4, 2012

(65) Prior Publication Data
US 2012/0219528 A1 Aug. 30, 2012

Related U.S. Application Data

(60) Continuation of application No. 12/583,679, filed on Aug. 24, 2009, now Pat. No. 8,192,975, which is a continuation of application No. 10/862,036, filed on Jun. 4, 2004, now Pat. No. 7,598,070, which is a continuation of application No. 10/340,389, filed on Jan. 10, 2003, now Pat. No. 6,764,845, which is a division of application No. 09/453,317, filed on Dec. 2, 1999, now Pat. No. 6,759,050.

(60) Provisional application No. 60/110,689, filed on Dec. 3, 1998.

(51) Int. Cl.
| | |
|---|---|
| A61K 39/23 | (2006.01) |
| A61K 48/00 | (2006.01) |
| C12N 7/01 | (2006.01) |
| C12N 15/864 | (2006.01) |
| A61K 47/26 | (2006.01) |
| A61K 47/10 | (2006.01) |
| A61K 38/48 | (2006.01) |
| C12N 15/86 | (2006.01) |
| A61K 9/00 | (2006.01) |

(52) U.S. Cl.
CPC ............... *C12N 15/86* (2013.01); *A61K 47/26* (2013.01); *A61K 47/10* (2013.01); *C12N 2750/14151* (2013.01); *A61K 38/4846* (2013.01); *A61K 48/00* (2013.01); *A61K 9/0019* (2013.01); *C12N 2750/14143* (2013.01)
USPC .................. 424/199.1; 424/278.1; 424/233.1; 424/93.2; 435/235.1; 435/260

(58) Field of Classification Search
CPC ....... A61K 47/10; A61K 47/26; A61K 48/00; C12N 15/86; C12N 2750/14143; C12N 2750/14151
See application file for complete search history.

(56) References Cited

U.S. PATENT DOCUMENTS

| | | | |
|---|---|---|---|
| 4,587,027 A | 5/1986 | Preusch et al. | |
| 5,616,487 A | 4/1997 | Palsson et al. | |
| 5,651,916 A | 7/1997 | Weir | |
| 5,763,395 A | 6/1998 | Blackburn et al. | |
| 5,780,295 A | 7/1998 | Levesey et al. | |
| 5,789,390 A | 8/1998 | Descamps et al. | |
| 6,110,456 A * | 8/2000 | During | 424/93.2 |
| 6,194,136 B1 | 2/2001 | Levesey et al. | |
| 6,521,225 B1 * | 2/2003 | Srivastava et al. | 424/93.2 |
| 6,566,118 B1 * | 5/2003 | Atkinson et al. | 435/239 |
| 6,759,050 B1 * | 7/2004 | Sista et al. | 424/199.1 |
| 6,764,845 B2 * | 7/2004 | Sista et al. | 435/235.1 |
| 6,797,505 B2 * | 9/2004 | Snyder et al. | 435/235.1 |
| 7,598,070 B2 * | 10/2009 | Sista et al. | 435/235.1 |
| 8,192,975 B2 * | 6/2012 | Sista et al. | 435/235.1 |

FOREIGN PATENT DOCUMENTS

| | | |
|---|---|---|
| WO | WO 98/02522 | 1/1998 |
| WO | WO 98/09524 | 3/1998 |

OTHER PUBLICATIONS

Adebayo, et al., "Stability of 17D Yellow Fever Virus Vaccine Using Different Stabilizers," *Biologicals* 26:309-316 (1998).
Cajavec, et al., "Tween 80-Solubilized Newcastle Disease Virus Prepared as a Water-In-Oil-In-Water Vaccine," *Avian Dis* 40(1):193-201 (1996).
Chirico, et al., "Optimization of Packaging of Adeno-Associated Virus Gene Therapy Vectors Using Plasmid Transfections," *J Virol Meth* 76:31-41 (1998).

* cited by examiner

*Primary Examiner* — Mary E Mosher
(74) *Attorney, Agent, or Firm* — Roberta L. Robins; Robins Law Group

(57) ABSTRACT

Stable pharmaceutical compositions comprising recombinant adeno-associated virus (AAV) virions are described. The compositions provide protection against loss of recombinant AAV vector genomes and transduceability under conditions such as exposure to cycles of freezing and thawing and storage in glass or polypropylene vials. The compositions comprise recombinant AAV virions in combination with one or more dihydric or polyhydric alcohols, and, optionally, a detergent, such as a sorbitan ester. Also described are methods of using the compositions.

16 Claims, 11 Drawing Sheets
(11 of 11 Drawing Sheet(s) Filed in Color)

EXCIPIENTS FOR USE IN ADENO-ASSOCIATED VIRUS PHARMACEUTICAL FORMULATIONS, AND PHARMACEUTICAL FORMULATIONS MADE THEREWITH

CROSS-REFERENCE TO RELATED APPLICATION

This application is a continuation of U.S. Ser. No. 12/583,679, filed Aug. 24, 2009, now U.S. Pat. No. 8,192,975, which is a continuation of U.S. Ser. No. 10/862,036, filed Jun. 4, 2004, now U.S. Pat. No. 7,598,070, which is a continuation of U.S. Ser. No. 10/340,389, filed Jan. 10, 2003, now U.S. Pat. No. 6,764,845, which is a divisional application of U.S. Ser. No. 09/453,317, filed Dec. 2, 1999, now U.S. Pat. No. 6,759,050, from which applications priority is claimed pursuant to 35 U.S.C. §120. U.S. Ser. No. 09/453,317 claims the benefit under 35 U.S.C. §119(e)(1) to provisional patent application Ser. No. 60/110,689, filed Dec. 3, 1998. The above applications are incorporated herein by reference in their entireties.

TECHNICAL FIELD

The present invention relates generally to DNA delivery methods. More particularly, the invention relates to stable pharmaceutical formulations comprising recombinant adeno-associated virus (rAAV) virions that provide protection against loss of transduceability due to manipulation, storage, transport, and the like, of the formulation.

BACKGROUND

The commercialization of any chemical compound for use as a pharmaceutical agent requires careful consideration of the formulation in which the chemical compound will be prepared, packaged and stored. The formulation must, of course, be compatible with human and/or veterinary administration. The formulation must be such that the agent retains potency for an extended period of time. Indeed, the formulation itself must be stable over a long period of time. The formulation must be compatible with techniques used for its purification, as well as for the purification of the agent contained within the formulation. Ultimately, the formulation must be compatible with the material in which the agent will be stored. If the agent must be frozen for stability, it is preferable that the formulation provide some protection against inactivation or denaturation due to freeze-thaw. In addition, the formulation should provide a suitable milieu for various dilutions of the agent.

Typically, pharmaceutical agents are stored as lyophilized formulations in a sterile container. A pharmaceutical agent formulation may be lyophilized if it is stable in such a non-aqueous state. This is of particular importance if the formulation must be stored frozen, as lyophilization minimizes the deleterious sequelae that may occur when an aqueous preparation is frozen and subsequently thawed. A glass vial is typically used because of the compatibility of glass with presently used sterilization techniques.

Adeno-associated virus (AAV) is a virus that readily transduces many human tissue and cell types. Accordingly, AAV has been used for gene therapy and nucleic acid immunization. The use of AAV in these contexts requires consideration of the above pharmaceutical formulation requirements. For example, it would be preferred that an AAV-containing sample not be lyophilized because of the possibility that small amounts of virus could become aerosolized and inadvertently transduce an unintended host. However, because AAV is known to be stable wider a variety of conditions that would inactivate most viruses, particularly enveloped viruses, it was not previously believed that the preparation of AAV formulations would be problematic.

It was unexpected, therefore, to find that the activity of recombinant AAV (rAAV) virions dropped significantly depending on the formulation used for storage and the conditions to which the formulation was exposed. It has been found, for example, that the transduction activity of a rAAV formulation may depend on the nature of the container, the constituents of the formulation, the temperature of the formulation, as well as changes in temperature, and the concentration of the rAAV virions stored.

It would, therefore, be a significant advancement in the art to provide formulations for storing rAAV virions which would preserve the activity of the rAAV virions for extended periods of times in containers made of various materials, including glass.

DISCLOSURE OF THE INVENTION

The present invention is based on the discovery that various excipient compositions have a stabilizing effect on recombinant AAV virions, such that less rAAV vector genomes are lost and higher transduceability levels are achieved as compared with AAV compositions that lack the excipients described herein. Various forms of the different embodiments described herein can be combined.

In one embodiment, then, a pharmaceutical composition comprising rAAV virions is provided. The composition provides protection against loss of rAAV vector genomes and transduceability under conditions such as exposure to cycles of freezing and thawing and storage in glass or polypropylene vials. The composition comprises a dihydric or polyhydric alcohol, such as one or more of sorbitol, polyethylene glycol, propylene glycol, and, optionally, a detergent, such as a sorbitan ester.

In an additional embodiment, the pharmaceutical composition comprises rAAV virions in an amount sufficient to provide a therapeutic effect when given in one or more doses and sorbitol present at a concentration of about 1 wt. % to about 5 wt. % and a detergent present at a concentration of about 0.1 wt. % to about 1 wt. %, wherein the detergent is polyoxyethylenesorbitan monolaurate (TWEEN-20) or polyoxyethylenesorbitan monooleate (TWEEN-80).

In yet other embodiments, a method for protecting a recombinant AAV virion from loss of activity resulting from exposure of the virion to a cycle of freezing and thawing, is provided, as is a method for protecting a recombinant AAV virion from loss of activity resulting from storage of the virion in a glass vessel. The methods comprise admixing the virion with a virion-stabilizing composition comprising a dihydric or polyhydric alcohol. In particular embodiments, the alcohol is one or more alcohols selected from the group consisting of polyethylene glycol, propylene glycol and sorbitol. The compositions used in the methods optionally include a detergent, such as a sorbitan ester.

In particular embodiments, the compositions used in the methods comprise sorbitol and a sorbitan ester selected from the group consisting of polyoxyethylenesorbitan monolaurate (TWEEN-20) and polyoxyethylenesorbitan monooleate (TWEEN-80).

These and other embodiments of the subject invention will readily occur to those of ordinary skill in the art in view of the disclosure herein.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
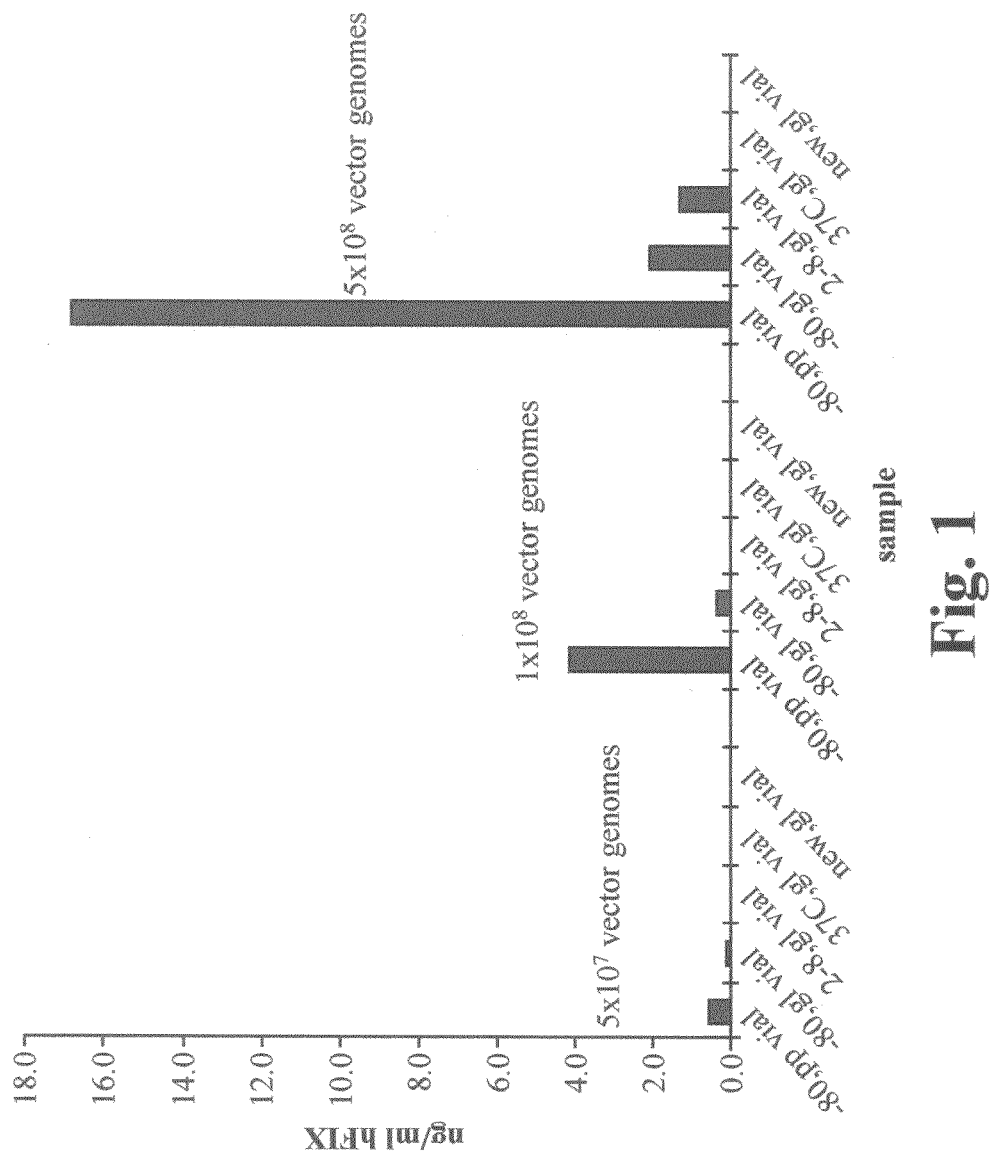
FIG. 1 is a bar graph illustrating the effect of temperature, vector dilution and storage in a glass vial on recombinant AAV vector (rAAV-hFIX) transduceability, as described in the examples. The numbers on the x axis represent the storage temperature; ppvial represents samples stored in a polypropylene vial and gl vial represents samples stored in glass.

The practice of the present invention will employ, unless otherwise indicated, conventional methods of virology, microbiology, molecular biology and recombinant DNA techniques within the skill of the art. Such techniques are explained fully in the literature. See, e.g., Sambrook et al. *Molecular Cloning: A Laboratory Manual* (Current Edition); *DNA Cloning: A Practical Approach*, Vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.); Freshney *Culture of Animal Cells, A Manual of Basic Technique* (Wiley-Liss, Third Edition); and Ausubel et al. (1991) *Current Protocols in Molecular Biology* (Wiley Interscience, NY).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. DEFINITIONS

In describing the present invention, the following terms will be employed, and are intended to be defined as indicated below.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "AAV vector" is meant a vector derived from an adeno-associated virus serotype, including without limitation, AAV-1, AAV-2, AAV-3, AAV-4, AAV-5, AAV-6, etc. AAV vectors can have one or more of the AAV wild-type genes deleted in whole or part, preferably the rep and/or cap genes (described below), but retain functional flanking ITR sequences (also described below). Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g.; by the insertion, deletion or substitution of nucleotides, so long as the sequences provide for functional rescue, replication and packaging.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a DNA molecule of interest which is flanked on both sides by AAV ITRs. An rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into recombinant virion particles for subsequent gene delivery.

The term "transfection" is used to refer to the uptake of foreign DNA by a cell. A cell has been "transfected" when exogenous DNA has been introduced inside the cell membrane. A number of transfection techniques are known in the art. See, e.g., Graham et al. (1973), *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via a replication-defective viral vector, such as via a recombinant AAV virion.

By "DNA" is meant a polymeric form of deoxyribonucleotides (adenine, guanine, thymine, or cytosine) in double-stranded or single-stranded form, either relaxed and supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence homologous to the mRNA). The term captures molecules that include the four bases adenine, guanine, thymine, or cytosine, as well as molecules that include base analogs which are known in the art.

A "gene" or "coding sequence" or a sequence which "encodes" a particular protein, is a nucleic acid molecule which is transcribed (in the case of DNA) and translated (in the case of mRNA) into a polypeptide in vitro or in vivo when placed under the control of appropriate regulatory sequences. The boundaries of the gene are determined by a start codon at the 5' terminus (corresponding to the amino terminal of the encoded protein) and a translation stop codon at the 3' (corresponding to the carboxy terminal of the encoded protein) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene that is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence and can be on the same (cis) or different (trans) nucleic acid molecule from the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3" or "5" relative to another sequence, it is to be understood that it is the position of the sequences in the "sense" or "coding" strand of a DNA molecule that is being referred to as is conventional in the art.

By "polyhydric alcohol" is meant an alcohol containing three or more hydroxyl groups. Generally, alcohols having three hydroxyl groups (trihydric) are glycerols, while those with more than three hydroxyl groups are sugar alcohols. A "dihydric alcohol" is one having two hydroxyl groups. Examples of polyhydric and dihydric alcohols are given below.

B. GENERAL METHODS

The present invention provides stable pharmaceutical compositions comprising rAAV virions. The compositions remain stable and active even when subjected to freeze/thaw cycling and when stored in containers made of various materials, including glass.

Recombinant AAV virions containing a heterologous nucleotide sequence of interest can be used for gene delivery, such as in gene therapy applications, for the production of transgenic animals, in nucleic acid vaccination, ribozyme and antisense therapy, as well as for the delivery of genes in vitro, to a variety of cell types.

Generally, rAAV virions are introduced into the cells of a subject using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with the cells e.g., in appropriate media, and screening for those cells harboring the DNA of interest using conventional techniques such as Southern blots and/or PCR, or by using selectable markers. Transduced cells can then be formulated into pharmaceutical compositions, described more fully below, and the composition introduced into the subject by various routes, such as by intramuscular, intravenous, intra arterial, subcutaneous and intraperitoneal injection, or by injection into smooth muscle, using e.g., a catheter, or directly into an organ.

For in vivo delivery, the rAAV virions will be formulated into a pharmaceutical composition and will generally be administered parenterally, e.g., by intramuscular injection directly into skeletal muscle, intra articularly, intravenously or directly into an organ.

Appropriate doses will depend on the subject being treated (e.g., human or nonhuman primate or other mammal), age and general condition of the subject to be treated, the severity of the condition being treated, the mode of administration of the rAAV virions, among other factors. An appropriate effective amount can be readily determined by one of skill in the art.

Thus, a "therapeutically effective amount" will fall in a relatively broad range that can be determined through clinical trials. For example, for in vivo injection, i.e., injection directly to the subject, a therapeutically effective dose will be on the order of from about $10^5$ to $10^{16}$ of the rAAV virions, more preferably $10^8$ to $10^{14}$ rAAV virions. For in vitro transduction, an effective amount of rAAV virions to be delivered to cells will be on the order of $19^5$ to $10^{13}$, preferably $10^8$ to $10^{13}$ of the rAAV virions. If the composition comprises transduced cells to be delivered back to the subject, the amount of transduced cells in the pharmaceutical compositions will be from about $10^4$ to $10^{10}$ cells, more preferably $10^5$ to $10^8$ cells. The dose, of course, depends on the efficiency of transduction, promoter strength, the stability of the message and the protein encoded thereby, etc. Effective dosages can be readily established by one of ordinary skill in the art through routine trials establishing dose response curves.

Dosage treatment may be a single dose schedule or a multiple dose schedule to ultimately deliver the amount specified above. Moreover, the subject may be administered as many doses as appropriate. Thus, the subject may be given, e.g., $10^5$ to $10^{16}$ rAAV virions in a single dose, or two, four, five, six or more doses that collectively result in delivery of, e.g., $10^5$ to $10^{16}$ rAAV virions. One of skill in the art can readily determine an appropriate number of doses to administer.

Pharmaceutical compositions will thus comprise sufficient genetic material to produce a therapeutically effective amount of the protein of interest, i.e., an amount sufficient to reduce or ameliorate symptoms of the disease state in question or an amount sufficient to confer the desired benefit. Thus, rAAV virions will be present in the subject compositions in an amount sufficient to provide a therapeutic effect when given in one or more doses. The rAAV virions can be provided as lyophilized preparations and diluted in the virion-stabilizing compositions for immediate or future use. Alternatively, the rAAV virions may be provided immediately after production and stored for future use.

The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

Preferred excipients confer a protective effect on the rAAV virion such that loss of rAAV virions, as well as transduceability resulting from formulation procedures, packaging, storage, transport, and the like, is minimized. These excipient compositions are therefore considered "virion-stabilizing" in the sense that they provide higher rAAV virion titers and higher transduceability levels than their non-protected counterparts, as measured using standard assays, such as the assays described in the experimental section. These Compositions therefore demonstrate "enhanced transduceability levels" as compared to compositions lacking the particular excipients described herein, and are therefore more stable than their non-protected counterparts.

Excipients that are used to protect the rAAV virion from activity degradative conditions include, but are not limited to, detergents, proteins, e.g., ovalbumin and bovine serum albumin, amino acids, e.g., glycine, polyhydric and dihydric alcohols, such as but not limited to polyethylene glycols (PEG) of varying molecular weights, such as PEG-200, PEG-400, PEG-600, PEG-1000, PEG-1450, PEG-3350, PEG-6000, PEG-8000 and any molecular weights in between these values, with molecular weights of 1500 to 6000 preferred, propylene glycols (PG), sugar alcohols, such as a carbohydrate, preferably, sorbitol. The detergent, when present, can be an anionic, a cationic, a zwitterionic or a nonionic detergent. A preferred detergent is a nonionic detergent. More preferably, the nonionic detergent is a sorbitan ester, e.g., polyoxyethylenesorbitan monolaurate (TWEEN-20) polyoxyethylenesorbitan monopalmitate (TWEEN-40), polyoxyethylenesorbitan monostearate (TWEEN-60), polyoxyethylenesorbitan tristearate (TWEEN-65), polyoxyethylenesorbitan monooleate (TWEEN-80), polyoxyethylenesorbitan trioleate (TWEEN-85), preferably TWEEN-20 and/or TWEEN-80. These excipients are commercially available from a number of vendors, such as Sigma, St. Louis, Mo.

The amount of the various excipients present will vary and is readily determined by one of skill in the art. For example, a protein excipient, such as BSA, if present, will generally be present at a concentration of between 1.0 wt. % to about 20 wt. %, preferably 10 wt. %. If an amino acid such as glycine is used in the formulations, it will generally be present at a concentration of about 1 wt. % to about 5 wt. %. A carbohydrate, such as sorbitol, if present, will be present at a concentration of about 0.1 wt % to about 10 wt. %, preferably between about 0.5 wt. % to about 15 wt. %, more preferably about 1 wt. % to about 5 wt. %. If PEG is present, it will generally be present on the order of about 2 wt. % to about 40 wt. %, preferably about 10 wt. % top about 25 wt. %. If propylene glycol is used in the subject formulations, it will typically be present at a concentration of about 2 wt. % to about 60 wt. %, preferably about 5 wt. % to about 30 wt. %. If a detergent such as a sorbitan ester (TWEEN) is present, it will generally be present at a concentration of about 0.05 wt. % to about 5 wt. %, preferably between about 0.1 wt. % and about 1 wt %.

In one preferred embodiment, an aqueous virion-stabilizing formulation comprises a carbohydrate, such as sorbitol, at a concentration of between 0.1 wt. % to about 10 wt. %, preferably between about 1 wt. % to about 5 wt. %, and a detergent, such as a sorbitan ester (TWEEN) at a concentration of between about 0.05 wt. % and about 5 wt. %, preferably between about 0.1 wt. % and about 1 wt. %. Virions are generally present in the composition in an amount sufficient to provide a therapeutic effect when given in one or more doses, as defined above.

C. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

MATERIALS AND METHODS

Production of Recombinant AAV Virions

Recombinant AAV virions can be produced using the method described in commonly owned U.S. Pat. No. 5,622,856 to Natsoulis, the disclosure of which is incorporated herein by reference.

Briefly, the method includes the steps of: introducing an AAV vector into a suitable host cell; introducing an AAV helper construct into the host cell to express essential AAV helper functions; expressing viral helper functions in the host cell; and culturing the cell to produce rAAV virions. The AAV vector and AAV helper constructs can be transfected into the host cell, either sequentially or simultaneously, using techniques known to those of skill in the art. The expression of viral helper functions can be provided by infecting the host cell with a suitable helper virus selected from the group of adenoviruses, herpes viruses and vaccinia viruses. The viral helper functions transactivate AAV promoters present in the AAV helper construct that direct the transcription and translation of AAV rep and cap regions. Thus, rAAV virions harboring a selected heterologous nucleotide sequence are formed and can be purified from the preparation using known.

The supernatant obtained from the host cell is titered for rAAV viral production either by dot blot to calculate the number of viral genomes or by transducing cells with the rAAV thus produced and harvested, and assaying for β-galactosidase activity to determine functional units as indicating rAAV LacZ transduceability. Transducing vector titers can be determined by infecting 293 cells, or any cell competent for transfection with AAV, with a dilution series of the rAAV virions. After 24 hours, the cells are fixed and stained with X-Gal. Sanes et al. (1986) *EMBO* 5:3133-3142. The titer is calculated by quantifying the number of blue cells.

Construction of pAAVLacZ

An AAV vector carrying the lacZ gene (pAAV-lacZ) was constructed as follows. The AAV coding region of pSub201 (Samulski et al. (1987) *J. Virol* 61:3096-3101), between the XbaI sites, was replaced with EcoPI linkers, resulting in plasmid pAS203. The EcoPI to HindIII fragment of pCMVβ (CLONETECH) was rendered blunt ended and cloned in the Klenow treated EcoRI site of pAS203 to yield pAAV-lacZ.

EXAMPLE 1

Effect of Freezing/Thaw Cycle on Recombinant AAV Activity

This experiment was done to determine the effect of a freeze/thaw cycle on rAAV activity. As shown in the table, about 75% of the activity is lost if no agent is added to the rAAV before it is frozen. The addition of bovine serum albumin (BSA) or polyoxyethylenesorbitan monolaurate (TWEEN-20) alone improved the recovery (about 50%). Sorbitol, however, completely protected the sample from freeze/thaw inactivation. These experiments were performed in polypropylene vials.

AAV-lacZ was chromatographed on an ion exchange column. A small volume from each of the fractions from the column was assayed for blue cell activity on the same day, prior to freezing the sample. The peak fraction contained 47% of the initial load on the column.

The remainder of each fraction was split into 4 portions and the following excipients added to each portion:

Portion a—no excipient;
Portion b—BSA to a final concentration of 10%;
Portion c—sorbitol to a final concentration of 5%;
Portion d—TWEEN-20 to a final concentration of 0.5%;

These samples were frozen, thawed a few days later and assayed for blue cell activity. The results are summarized in Table 1.

TABLE 1

| Sample | Excipient | % Yield |
|---|---|---|
| Active fraction, pre-freeze | None | 47% |
| Active fraction, post freeze-thaw | None | 15% |
| Active fraction, post freeze-thaw | BSA | 27% |
| Active fraction, post freeze-thaw | Sorbitol | 52% |
| Active fraction, post freeze-thaw | TWEEN-20 | 29% |

These results indicate that a single freeze/thaw cycle can result in a significant reduction in rAAV activity. This reduction in activity can be abrogated by addition of protective agents such as proteins, polyhydric alcohols and detergents, all of which are believed to act by different mechanisms. In this experiment, sorbitol had the greatest protective effect; essentially no loss of activity following freezing and thawing was observed in the sorbitol-containing sample.

EXAMPLE 2

Effect of Vector Dilution, Temperature and Storage in Glass Vials on Recombinant AAV Activity Initial stability experiments were conducted to determine the effect of vector dilution, recovery from polypropylene (pp) vials and glass (gl) vials and the effect of temperature (−80° C., 2-8° C., 37° C.) on storage stability and the effect of the addition of sorbitol on stability and recovery.

Samples of rAAV in a 1% sorbitol solution in phosphate buffered saline (PBS) were assayed undiluted as well as diluted 1-fold to about 10-fold (1.25 ml-12.5 ml) within 1% sorbitol/DPBS buffer. 0.5 ml aliquots of each member of the dilution series were placed in different storage conditions.

Following freezing, the samples were thawed and analyzed for vector genomes and for transduceability as described in Example 1. For transduceability studies, the vector genome titer used in the experiment was calculated using the starting concentration of undiluted vector. Each sample was diluted in complete Dulbecco's Modified Eagle Medium (DMEM) such that $1 \times 10^8$ or $5 \times 10^8$ vector genomes could be added to 298-BEK cells in a volume of 10 to 20 μL.

The stability-indicating assay used was loss of transduceability. Loss of transduceability was measured by human factor IX protein (hFIX) production following transduction with rAAV of 293 human embryonic kidney (HEK) cells. In this assay, different amounts of rAAV-hFIX vector were added to HEK cells and the ability to transduce was measured. The factor IX protein produced and secreted as a consequence of infection was measured using an ELISA technique. The results are reported in ng/mL of human factor IX protein (hFIX).

As can be seen by the results depicted in FIG. 1, storing rAAV in glass regardless of the temperature that it was stored at caused the rAAV activity to drop. In this experiment it appears that activity and temperature are inversely related—i.e., the lower the temperature the higher the activity.

EXAMPLE 3

Effect of Storage in Glass on Recombinant AAV Activity

The results of the experiment described in Example 2 indicate that storage of rAAV in glass resulted in a loss of activity. This experiment was designed to examine whether this was due merely to the fact that rAAV was adsorbed to the glass vial.

In order to rule out this possibility, the number of genomes (the number of DNA molecules encapsulated in AAV as determined by Southern Blot dot) added to the glass and polypropylene vials was determined. The rAAV was allowed to sit in the glass and polypropylene vials in various formulations and temperatures. Two aliquots of rAAV virus were taken: the first used to recount the number of genomes recovered and the second to determine activity (functional units as opposed to genomes) as determined in Example 1. The results indicate that when rAAV is stored in glass the activity drops significantly. This occurs at various dilutions of rAAV.

rAAV samples were frozen undiluted as well as diluted 5-fold, 50-fold or 100-fold. The diluent used was such that the final concentration of sorbitol was either 5% or 1%. Duplicate samples were placed in glass vials and polypropylene tubes. Samples were placed at −80° C. or at ambient temperature. Following freezing, the samples were thawed and analyzed for vector genomes and for transduceability as described above. For transduceability studies, the vector genome titer used in the experiment was calculated using the starting concentration of undiluted vector. Each sample was diluted in complete DMEM such that $1\times10^8$ or $5\times10^8$ vector genomes could be added to 293-HEK cells in a volume of 10 to 20 μL.

The stability-indicating assays used were loss of vector genomes and loss of transduceability. Loss of vector genomes was measured using a dot blot assay. This assay involves extraction of vector DNA from the sample, denaturing the DNA, and loading it on a nylon membrane. By hybridizing this DNA to a complimentary radioactive DNA probe, the number of vector genomes can be calculated by comparison to a standard. Loss, of transduceability was measured as described in Example 2.

Table 2 lists the data obtained for 293-HEK cells transduced with $1\times10^8$ vector genomes. The data is shown for the samples incubated at −80° C. Column 2 shows the transduceability, column 3 is the measured vector genomes/ml and column 4 is the data in column 3 multiplied by the dilution factor. In the table, "ppS" indicates polypropylene stock container and "ppC" indicates polypropylene container.

TABLE 2

| 1 Sample | 2 ng/ml hFIX | 3 Vector Genomes/ml | 4 Normalized Vector Genomes |
|---|---|---|---|
| 5%, ppS, −80° C., stock | 11.6 | $1.5 \times 10^{12}$ | $1.5 \times 10^{12}$ |
| 5%, ppC, −80° C., 1:5 | 6.6 | $2.3 \times 10^{11}$ | $1.2 \times 10^{12}$ |
| 5%, glass, −80° C., 1:5 | 3.8 | $1.9 \times 10^{11}$ | $9.5 \times 10^{11}$ |
| 1%, ppC, −80° C., 1:5 | 4.2 | $1.9 \times 10^{11}$ | $9.5 \times 10^{11}$ |
| 1%, glass, −80° C., 1:5 | 2.1 | $1.7 \times 10^{11}$ | $8.5 \times 10^{11}$ |
| 5%, ppC., −80° C., 1:50 | 5.9 | $2.5 \times 10^{10}$ | $1.3 \times 10^{12}$ |
| 5%, glass, −80° C., 1:50 | 4.5 | $1.5 \times 10^{10}$ | $7.5 \times 10^{11}$ |
| 1%, ppC, −80° C., 1:50 | 4.3 | $1.7 \times 10^{10}$ | $8.5 \times 10^{11}$ |
| 1%, glass, −80° C., 1:50 | 4.6 | $1.9 \times 10^{10}$ | $9.5 \times 10^{11}$ |
| 5%, ppC, −80° C., 1:100 | 5.5 | $1.5 \times 10^{10}$ | $1.5 \times 10^{12}$ |
| 5%, glass, −80° C., 1:100 | 4.0 | $9.3 \times 10^{9}$ | $9.3 \times 10^{11}$ |
| 1%, ppC, −80° C., 1:100 | 4.6 | $1.2 \times 10^{10}$ | $1.2 \times 10^{12}$ |
| 1%, glass, −80° C., 1:100 | 2.4 | $1.1 \times 10^{10}$ | $1.1 \times 10^{12}$ |

Figure 2:
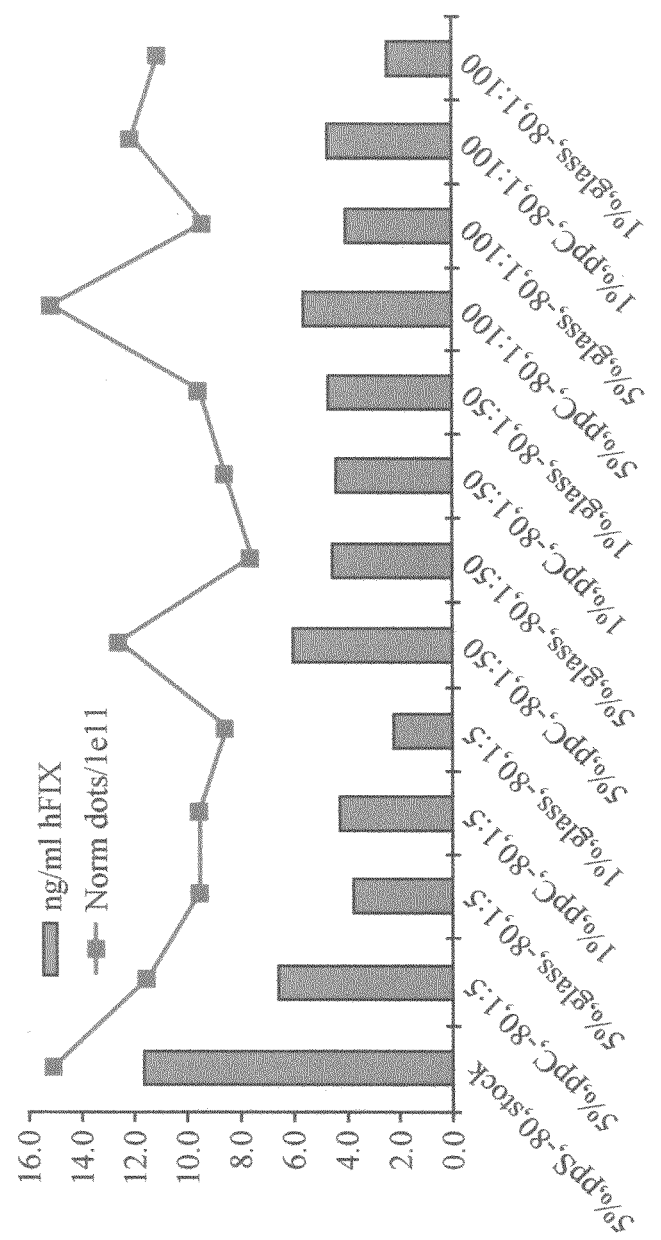
FIG. 2 depicts the results of experiments conducted as described in Example 3 in which 293-HEK cells were transduced with $1 \times 10^8$ vector genomes using samples stored in polypropylene or glass, in 1% or 5% sorbitol, at various dilutions as specified. The bars represent ng/ml of rAAV-hFIX and the line graph above the bars represents data normalized for dilution.

FIG. 2 depicts the data for the vector genome and transduceability results in which $1\times10^8$ vector genomes were used for the transduceability assay. Vector genomes obtained experimentally have been normalized for the dilution to compare with the transduceability results. In addition, the vector genome results have been divided by $1\times10^{11}$ to produce manageable numbers for the graph.

Figure 3:
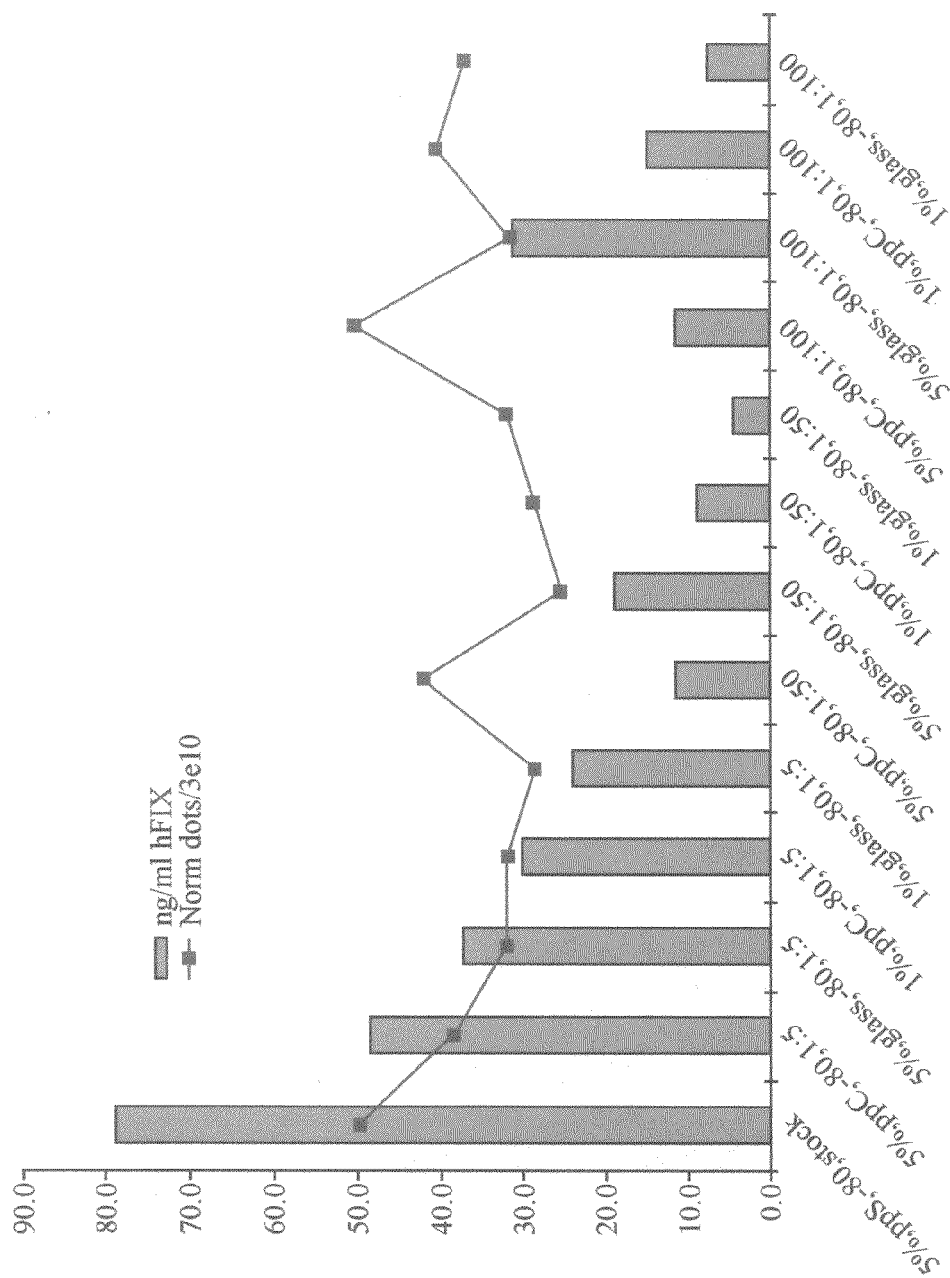
FIG. 3 depicts the results of experiments conducted as described in Example 3 in which 293-HEK cells were transduced with $5 \times 10^8$ vector genomes using samples stored in polypropylene or glass, in 1% or 5% sorbitol, at various dilutions as specified. The bars represent ng/ml of rAAV-hFIX and the line graph above the bars represents data normalized for dilution.

Table 3 and FIG. 3 depict the results of experiments conducted as described above except that the transduceability assay for 293-HEK cells transduced with $5\times10^8$ vector genomes.

TABLE 3

| 1 Sample | 2 ng/ml hFIX | 3 Vector Genomes/ml | 4 Normalized Vector Genomes |
|---|---|---|---|
| 5%, ppS, −80° C., stock | 78.8 | $1.5 \times 10^{12}$ | $1.5 \times 10^{12}$ |
| 5%, ppC, −80° C., 1:5 | 48.3 | $2.3 \times 10^{11}$ | $1.2 \times 10^{11}$ |
| 5%, glass, −80° C., 1:5 | 37.1 | $1.9 \times 10^{11}$ | $9.5 \times 10^{11}$ |

TABLE 3-continued

| 1 Sample | 2 ng/ml hFIX | 3 Vector Genomes/ml | 4 Normalized Vector Genomes |
|---|---|---|---|
| 1%, ppC, −80° C., 1:5 | 29.9 | $1.9 \times 10^{11}$ | $9.5 \times 10^{11}$ |
| 1%, glass, −80° C., 1:5 | 23.9 | $1.7 \times 10^{11}$ | $8.5 \times 10^{11}$ |
| 5%, ppC., −80° C., 1:50 | 11.3 | $2.5 \times 10^{10}$ | $1.3 \times 10^{12}$ |
| 5%, glass, −80° C., 1:50 | 18.5 | $1.5 \times 10^{10}$ | $7.5 \times 10^{11}$ |
| 1%, ppC, −80° C., 1:50 | 8.6 | $1.7 \times 10^{10}$ | $8.5 \times 10^{11}$ |
| 1%, glass, −80° C., 1:50 | 4.2 | $1.9 \times 10^{10}$ | $9.5 \times 10^{11}$ |
| 5%, ppC, −80° C., 1:100 | 11.2 | $1.5 \times 10^{10}$ | $1.5 \times 10^{12}$ |
| 5%, glass, −80° C., 1:100 | 30.7 | $9.3 \times 10^{9}$ | $9.3 \times 10^{11}$ |
| 1%, ppC, −80° C., 1:100 | 14.5 | $1.2 \times 10^{10}$ | $1.2 \times 10^{12}$ |
| 1%, glass, −80° C., 1:100 | 7.1 | $1.1 \times 10^{10}$ | $1.1 \times 10^{12}$ |

Figure 4:
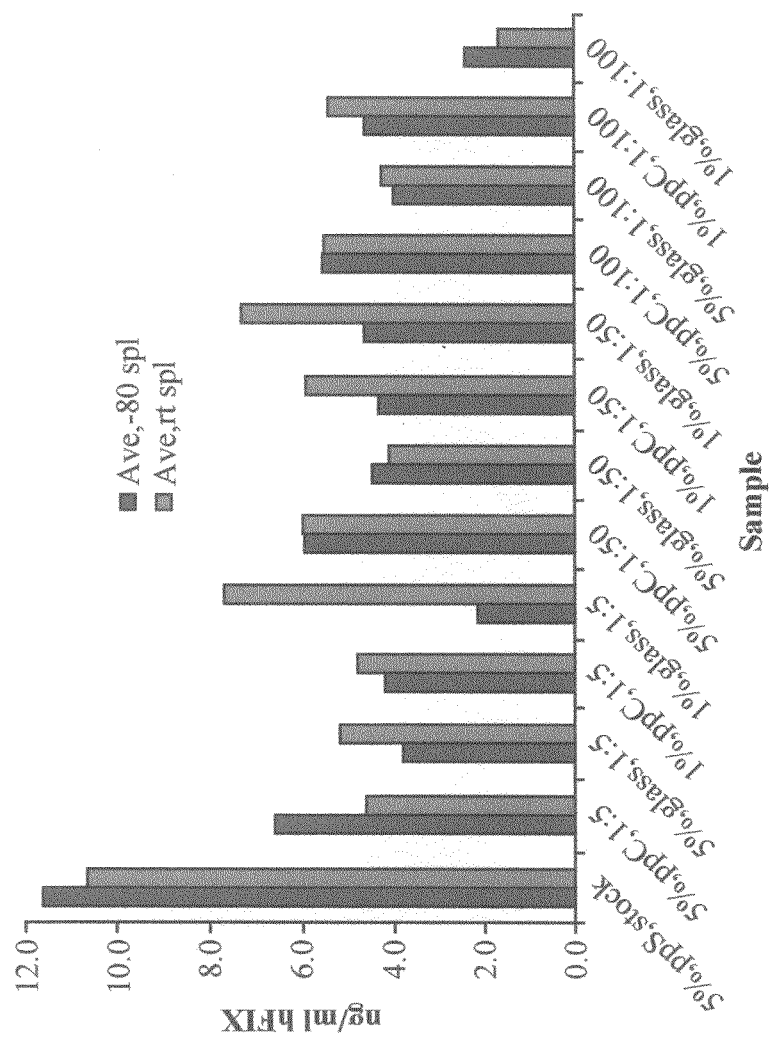
FIG. 4 depicts the results of experiments conducted at $-80°$ C. or ambient (room) temperature for vector genome count and transduceability assay in which transduction was done using $1 \times 10^8$ vector genomes as described in Example 3. Maroon bars represent results of experiments done at room temperature and light blue bars represent experiments done at $-80°$ C.
Figure 5:
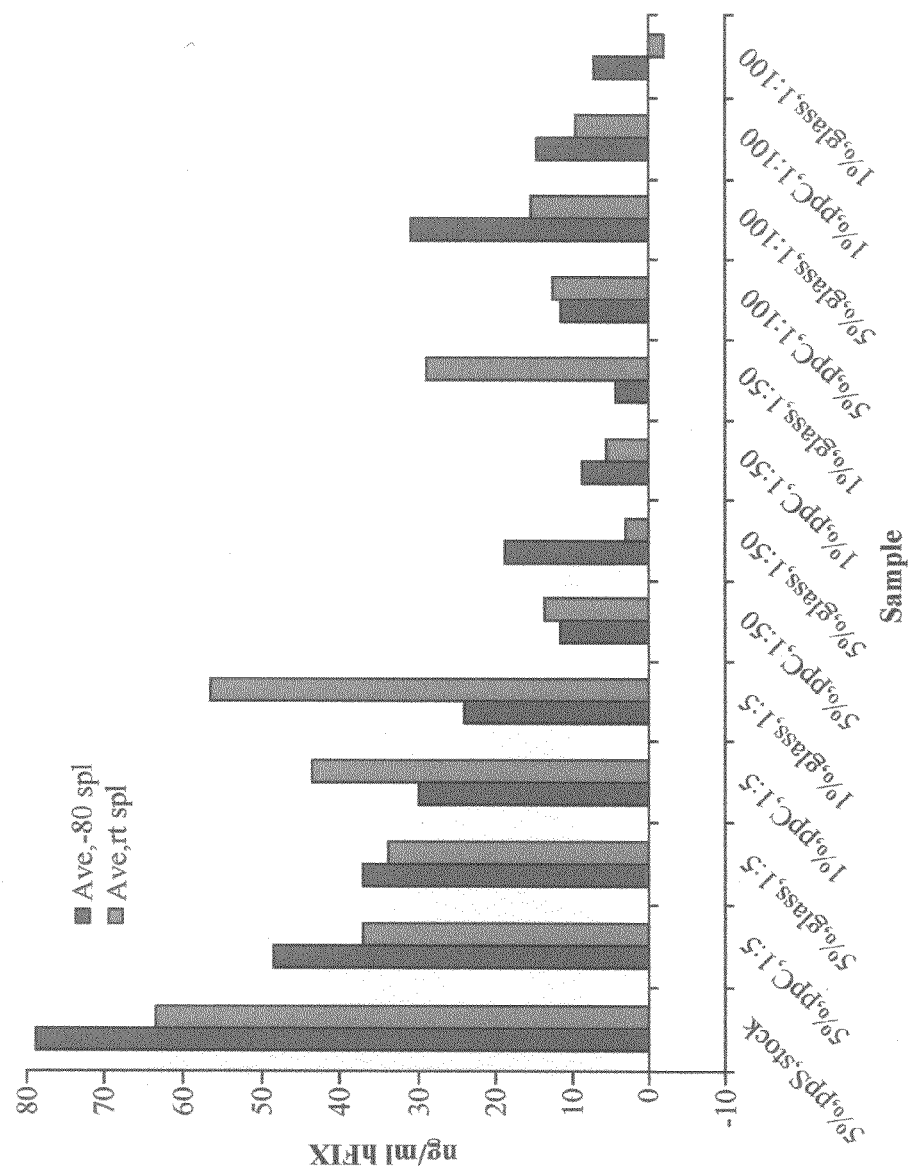
FIG. 5 depicts the results of experiments conducted at $-80°$ C. or ambient (room) temperature for vector genome count and transduceability assay in which transduction was done using $5 \times 10^8$ vector genomes as described in Example 3. Maroon bars represent results of experiments done at room temperature and light blue bars represent experiments done at $-80°$ C.

FIG. 4 and FIG. 5 depict the results of experiments conducted at −80° C. or ambient temperature for vector genome count and transduceability assay in which transduceability was done using $1\times10^8$ vector genomes (FIG. 4) and $5\times10^8$ vector genomes (FIG. 5.)

These results from the transduceability experiments indicate that as the vector is diluted it decreases in infective capability. It can also be seen that samples prepared in 1% sorbitol have reduced transduceability compared to those prepared in 5% sorbitol. The results also indicate that storage in glass at −80° C. results in reduced transduceability compared to polypropylene.

Thus, it appears that there can be a physical loss of vector in the container under the conditions examined in these experiments. However, from the vector genome data it can be observed that there is no observable change in the number of vector genomes. The % correlation of variance (% CV) in the range of vector genomes (see Tables 2 and 3) is 22.4, well within the variability of the dot blot assay. However, the % CV for the transduceability for both titers, i.e., $1\times10^8$ vector genomes and $5\times10^8$ vector genomes, is greater than the variability of the transduceability assay (about 30%). Accordingly, it appears that, rather than a loss in vector genome number, the vector per se is losing transduceability.

EXAMPLE 4

The Effect of Added Excipients on the Stability of Recombinant AAV-I

These experiments were designed to study the effect of different formulations containing 1% sorbitol and various concentrations of TWEEN-20, TWEEN-80, polyethylene glycol (PEG), glycine and combinations thereof. Virus placed in growth media was used as a baseline. The tubes used throughout were polypropylene. The samples were maintained in the formulations for 1 hr at room temperature before transducing culture cells.

The stability of the AAV vector was measured using the loss of transduceability assay described in Example 2 to further explore the effect of added excipients. Samples were diluted in media or in the buffer excipient to give concentrations of $1\times10^8$, $5\times10^8$, $1\times10^9$ or $5\times10^9$ in 15 μL. Samples were placed in polypropylene tubes for about 1 hour and then used to transduce 293-HEK cells.

Figure 6:
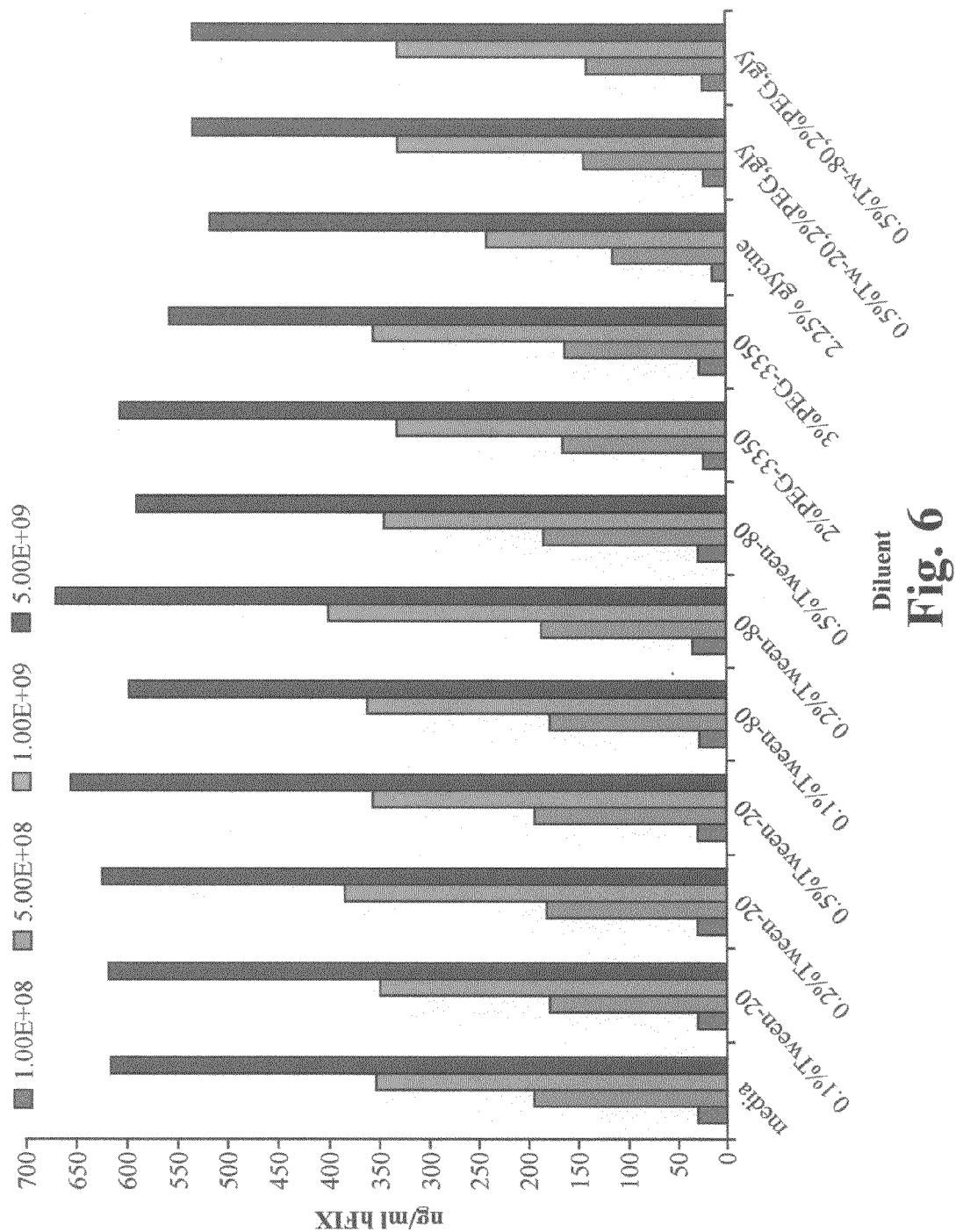
FIG. 6 depicts the results obtained in the experiment described in Example 4 using the parameters given in Table 4. Green bars represent experiments conducted using $1 \times 10^8$ vector genomes; red bars represent experiments conducted using $5 \times 10^8$ vector genomes; pink bars represent experiments conducted using $1 \times 10^9$ vector genomes; dark blue bars represent experiments conducted using $5 \times 10^9$ vector genomes.
Figure 7:
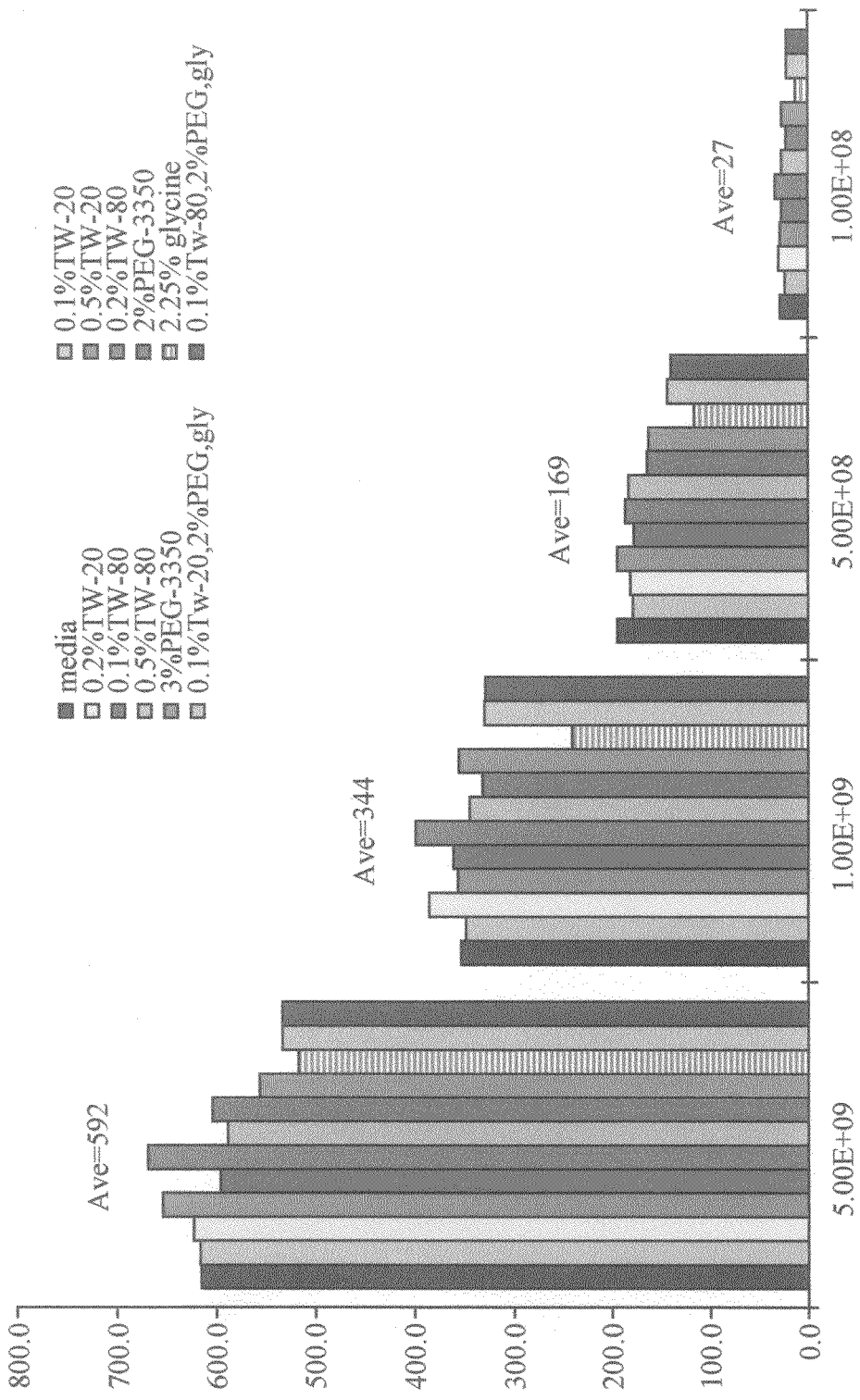
FIG. 7 depicts the results obtained in the experiment described in Example 4 using the parameters given in Table 4 and regraphed as vector genomes. Dark blue bars represent experiments conducted using media as the diluent; pink bars represent experiments conducted using 0.1% TWEEN-20 as the diluent; yellow bars represent experiments conducted using 0.2% TWEEN-20 as the diluent; red bars represent experiments conducted using 0.5% TWEEN-20 as the diluent; green bars represent experiments conducted using 0.1% TWEEN-80 as the diluent; brown bars represent experiments conducted using 0.2% TWEEN-80 as the diluent; lavender bars represent experiments conducted using 0.5% TWEEN-80 as the diluent; teal blue bars represent experiments conducted using 2% PEG-3350 as the diluent; turquoise blue bars represent experiments conducted using 3% PEG-3350 as the diluent; purple-striped bars represent experiments conducted using 2.25% glycine as the diluent; light blue bars represent experiments conducted using 0.1% TWEEN-20+2% PEG-3350+2.25% glycine as the diluent; blue bars represent experiments conducted using 0.1% TWEEN-80+2% PEG-3350+2.25% glycine as the diluent. In all cases, the excipient included 1% sorbitol.

The formulations of excipients and results are given in ng/ml of human factor IX in Table 4 and the results listed therein are depicted in FIG. 6 and FIG. 7. In all cases, the excipient included 1% sorbitol.

TABLE 4

| Diluent (All experimental excipients contained 1% Sorbitol) | Concentration (ng/ml) | | | |
|---|---|---|---|---|
| Media | 30.5 | 194.5 | 353.1 | 615.8 |
| 0.1% TWEEN-20 | 26.4 | 178.6 | 347.7 | 616.9 |
| 0.2% TWEEN-20 | 31.8 | 180.6 | 384.4 | 623.9 |
| 0.5% TWEEN-20 | 30.2 | 194.6 | 355.6 | 654.6 |
| 0.1% TWEEN-80 | 29.2 | 178.1 | 360.8 | 595.9 |
| 0.2% TWEEN-80 | 35.6 | 186.4 | 399.8 | 669.0 |
| 0.5% TWEEN-80 | 29.8 | 183.6 | 344.3 | 588.6 |
| 2% PEG-3350 | 25.0 | 164.5 | 331.5 | 604.4 |
| 3% PEG-3350 | 28.6 | 162.0 | 354.9 | 556.0 |
| 2.25% glycine | 14.9 | 115.6 | 240.8 | 516.3 |
| 0.1% TWEEN-20 + 2% PEG + 2.25% glycine | 23.5 | 143.5 | 329.9 | 533.1 |
| 0.1% TWEEN-80 + 2% PEG + 2.25% glycine | 24.0 | 140.6 | 329.5 | 532.3 |
| Particles/well | $1 \times 10^8$ | $5 \times 10^8$ | $1 \times 10^9$ | $5 \times 10^9$ |

These data indicate that the addition of TWEEN seems to have stabilized rAAV, and PEG and glycine do little and may even reduce the overall activity of rAAV.

EXAMPLE 5

The Effect of Added Excipients on the Stability of Recombinant AAV-II

Figure 8:
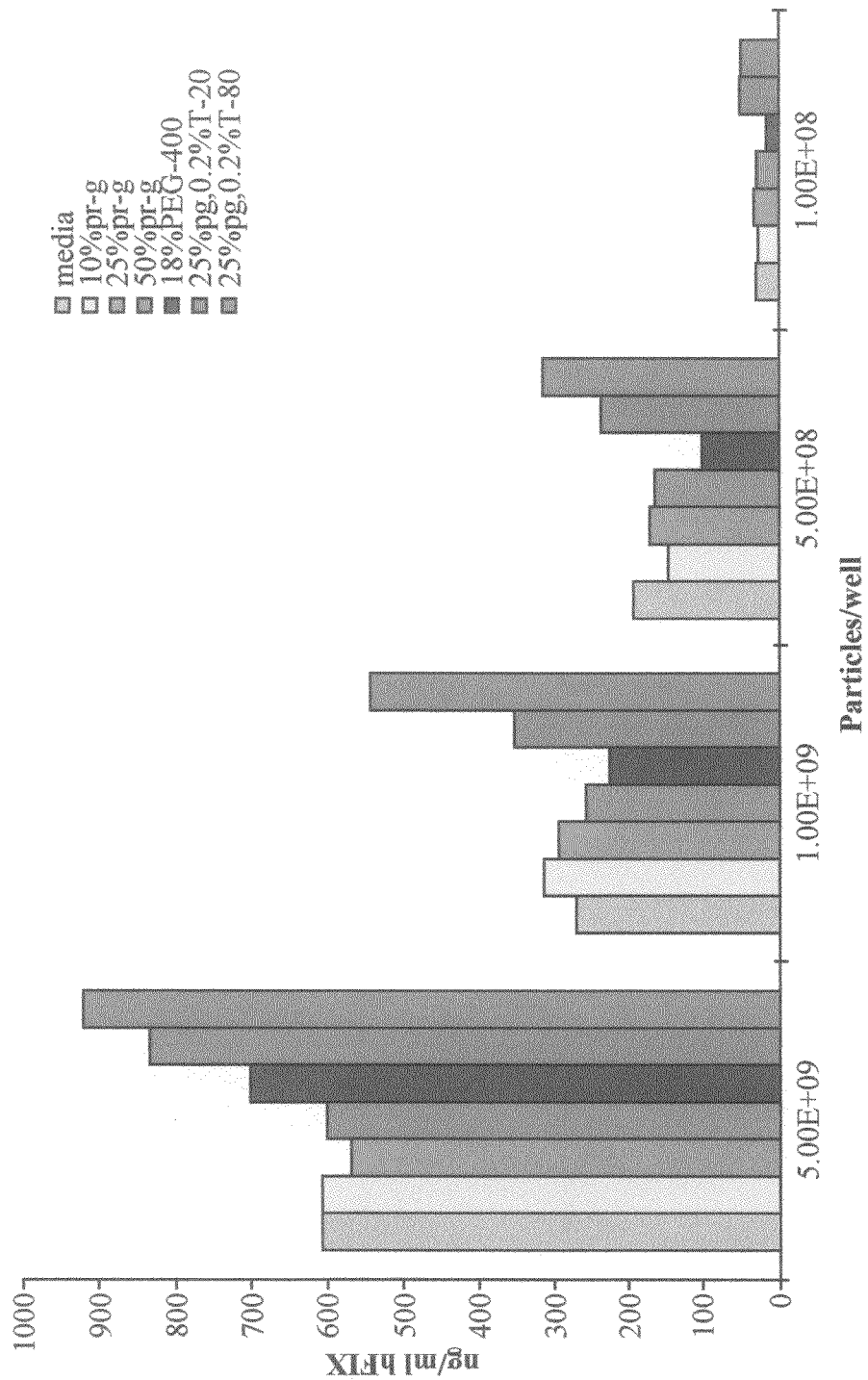
FIG. 8 depicts the results obtained in the experiment describe in Example 5 to determine the effect of formulation composition on the stability of recombinant AAV vectors using the parameters described in Table 5. Light blue bars represent experiments conducted using media as the diluent; yellow bars represent experiments conducted using 10% propylene glycol as the diluent; pink bars represent experiments conducted using 25% propylene glycol as the diluent; turquoise blue bars represent experiments conducted using 50% propylene glycol as the diluent; dark blue bars represent experiments conducted using 18% PEG-400 as the diluent; light brown bars represent experiments conducted using 25% propylene glycol+0.2% TWEEN-20 as the diluent; blue bars represent experiments conducted using 25% propylene glycol+0.2% TWEEN-80 as the diluent.

The stability of the AAV vector was measured as described in Example 4. The formulations of excipients and results are given in Table 5 and the results listed therein are depicted in FIG. 8. In all cases, the excipient included 1% sorbitol.

TABLE 5

| Diluent All experimental excipients contained 1% Sorbitol | Concentration (ng/ml) | | | |
|---|---|---|---|---|
| Media | 28.5 | 192.2 | 269.2 | 607.0 |
| 10% Propylene Glycol | 26.0 | 144.7 | 313.3 | 607.0 |
| 25% Propylene Glycol | 20.9 | 170.8 | 292.4 | 568.1 |
| 50% Propylene Glycol | 26.9 | 163.4 | 256.5 | 600.1 |
| 18% PEG-400 | 14.8 | 94.2 | 224.7 | 701.1 |
| 25% Propylene Glycol + 0.2% TWEEN-20 | 49.7 | 235.7 | 352.3 | 834.9 |
| 25% Propylene Glycol + 0.2% TWEEN-80 | 47.5 | 314.2 | 542.6 | 919.9 |
| Particles/well | $1 \times 10^8$ | $5 \times 10^8$ | $1 \times 10^9$ | $5 \times 10^9$ |

EXAMPLE 6

The Effect of Added Excipients on the Stability of Recombinant AAV: Comparison of Glass and Polypropylene Vials This experiment was designed to study the effect of 1% sorbitol and TWEEN-80 on the activity of rAAV stored in glass vials compared to the effect on activity of rAAV stored in polypropylene vials at two temperatures (4° C. and −80° C.).

Figure 9:
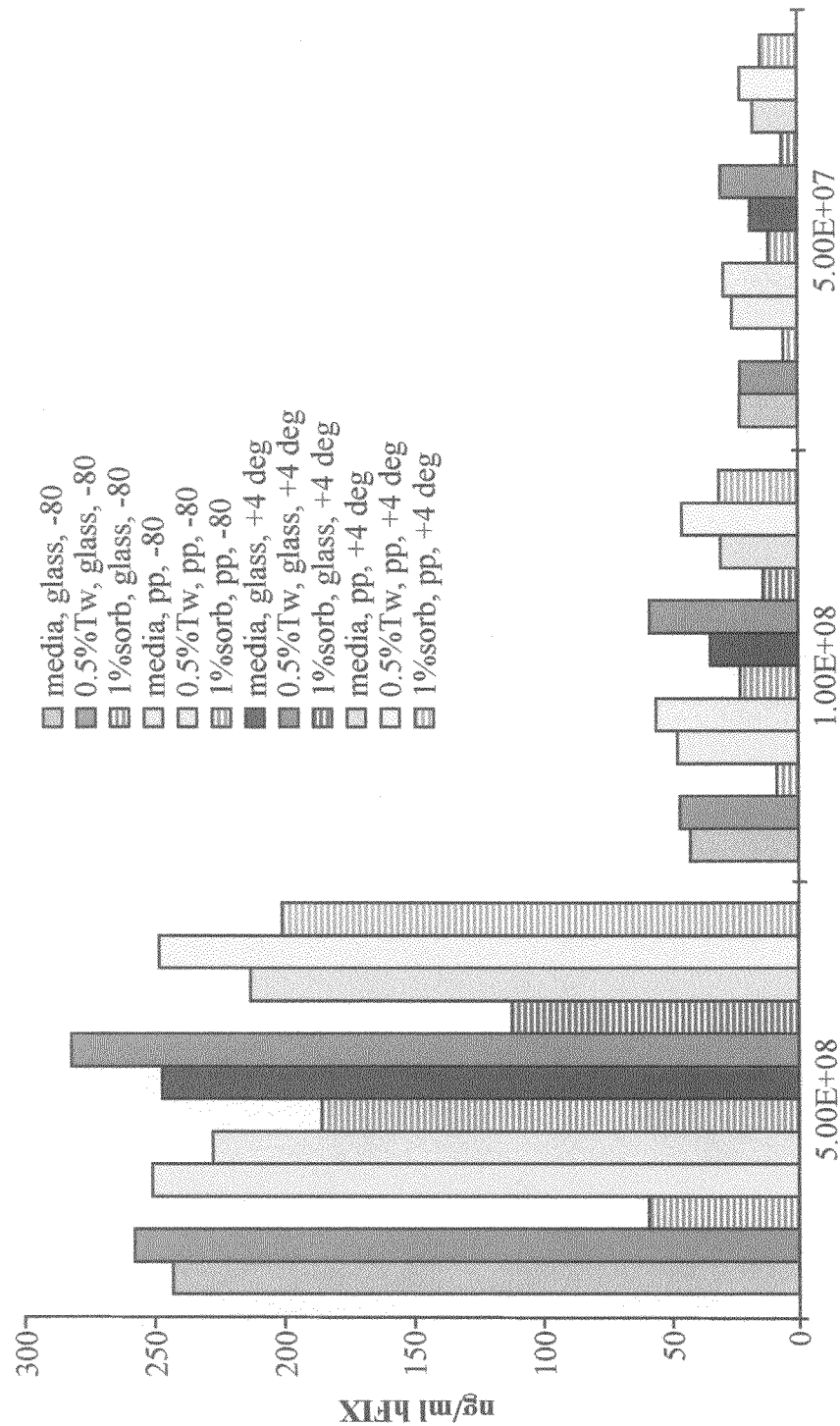
FIG. 9 depicts the results obtained in the experiment described in Example 6 to determine the effect of various excipients and storage conditions on the stability of recombinant AAV vectors, as described in Table 6. Light blue bars represent experiments conducted using media as the diluent and storage in glass at $-80°$ C.; red bars represent experiments conducted using 0.5% TWEEN-80 as the diluent and storage in glass at $-80°$ C.; green-striped bars represent experiments concluded using 1% sorbitol as the diluent and storage in glass at $-80°$ C.; yellow bars represent experiments conducted using media as the diluent and storage in polypropylene at $-80°$ C.; gray bars represent experiments conducted using 0.5% TWEEN-80 as the diluent and storage in polypropylene at $-80°$ C.; purple-striped bars represent experiments conducted using 1% sorbitol as the diluent and storage in polypropylene at $-80°$ C.; dark blue bars represent experiments conducted using media as the diluent and storage in glass at $+4°$ C.; blue bars represent experiments conducted using 0.5% TWEEN-80 as the diluent and storage in glass at $+4°$ C.; blue-striped bars represent experiments conducted using 1% sorbitol as the diluent and storage in glass at $+4°$ C.; mustard yellow bars represent experiments conducted using media as the diluent and storage in polypropylene at $+4°$ C.; light yellow bars represent experiments conducted using 0.5% TWEEN-80 as the diluent and storage in polypropylene at $+4°$ C.; pink-striped bars represent experiments conducted using 1% sorbitol as the diluent and storage in polypropylene at $+4°$ C.

The stability of the AAV vector was measured as described using 5×10⁷, 1×10⁸ or 5×10⁸ particles/well. Each sample was done in a glass vial (GV) or a polypropylene tube (PT), and stored at room temperature (+4° C.) or at −80° C. overnight. The formulations of excipients and results are given in Table 6 and the results listed therein are depicted in FIG. 9.

TABLE 6

| Diluent | Concentration (ng/ml) | | |
|---|---|---|---|
| Media, glass, −80° C. | 23.6 | 42.8 | 243.3 |
| 0.5% TWEEN-80, glass, −80° C. | 23.5 | 46.7 | 254.7 |
| 1% sorbitol, glass, −80° C. | 6.2 | 8.9 | 59.2 |
| Media, polypropylene, −80° C. | 26.4 | 48.1 | 251.1 |
| 0.5% TWEEN-80, polypropylene, −80° C. | 30.2 | 56.0 | 228.2 |
| 1% sorbitol, polypropylene, −80° C. | 12.2 | 23.3 | 185.9 |
| Media, glass, +4° C. | 19.7 | 34.9 | 247.1 |
| 0.5% TWEEN-80, glass, +4° C. | 31.1 | 58.7 | 282.2 |
| 1% sorbitol, glass, +4° C. | 7.0 | 14.5 | 111.9 |
| Media, polypropylene, +4° C. | 18.1 | 30.8 | 212.7 |
| 0.5% TWEEN-80, polypropylene, +4° C. | 23.3 | 46.6 | 248.6 |
| 1% sorbitol, polypropylene, +4° C. | 15.2 | 31.9 | 200.9 |
| Particles/well | $5 \times 10^7$ | $1 \times 10^8$ | $5 \times 10^8$ |

These data indicate that 1% sorbitol does not provide a significant protective effect for rAAV activity when stored in glass vials. When sorbitol is used alone, it provides a protective effect on rAAV stored in polypropylene vials. There is also an apparent protective effect when the sample is stored at 4° C. rather than at −80° C. The inclusion of TWEEN in the formulation reverses the reduced activity caused by storage of an rAAV sample in a glass vial.

EXAMPLE 7

Figure 10:
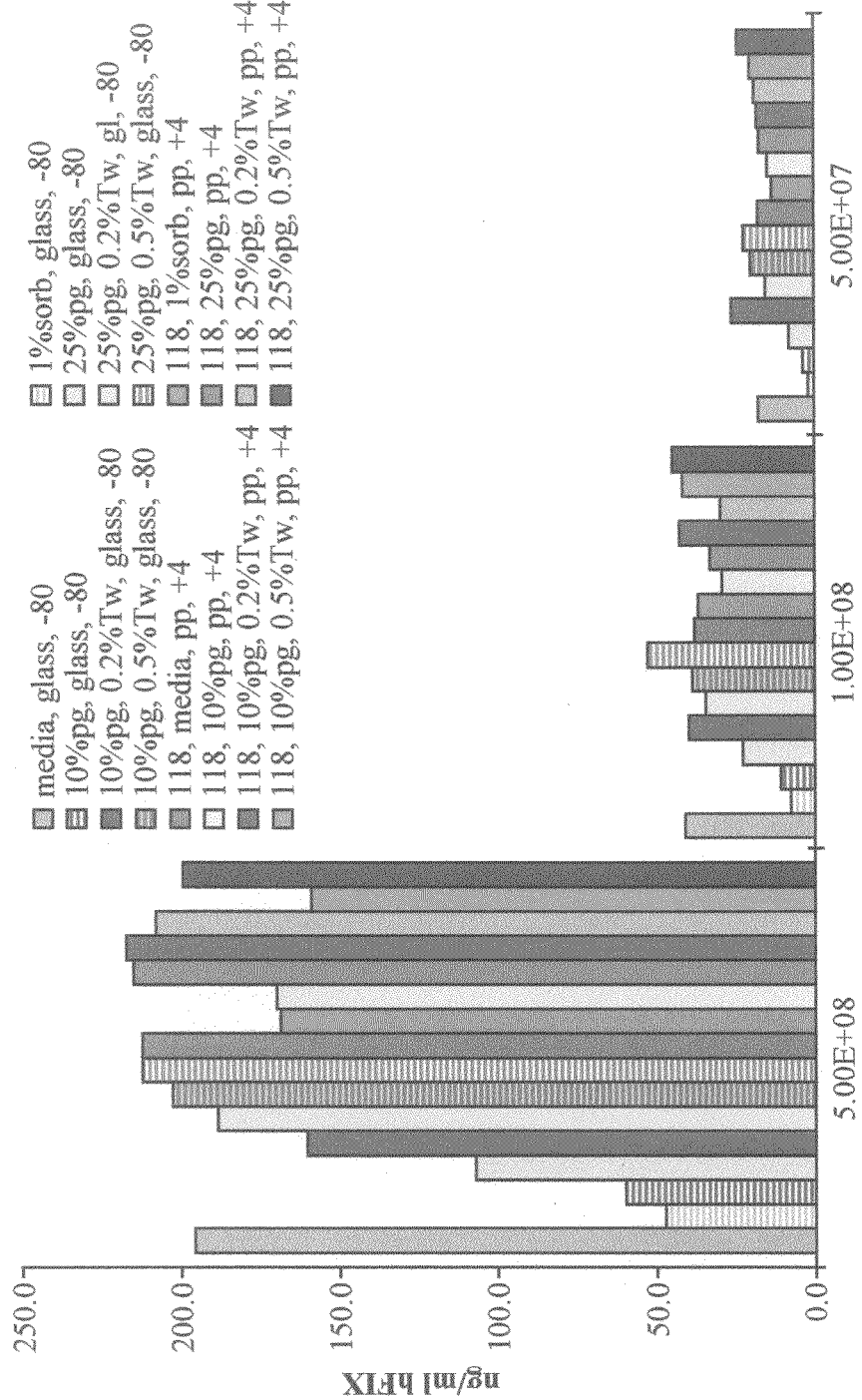
FIG. 10 depicts the results obtained in the experiment described in Example 7 to determine the effect of various excipients on loss of rAAV vector activity in samples stored in glass or polypropylene vials. Lavender bars represent experiments conducted using media as the diluent and storage in glass at $-80°$ C.; light blue-striped bars represent experiments conducted using 1% sorbitol as the diluent and storage in glass at $-80°$ C.; dark blue-striped bars represent experiments conducted using 10% propylene glycol (PG) as diluent and storage in glass at $-80°$ C.; gray bars represent experiments conducted using 25% PG as diluent and storage in glass at $-80°$ C.; blue bars represent experiments conducted using 10% PG+0.2% TWEEN-80 as diluent and storage in glass at $-80°$ C.; yellow bars represent experiments conducted using 25% PG+0.2% TWEEN-80 as diluent and storage in glass at $-80°$ C.; brown-striped bars represent experiments conducted using 10% PG+0.5% TWEEN-80 as diluent and storage in glass at $-80°$ C.; purple-striped bars represent experiments conducted using 25% PG+0.5% TWEEN-80 as diluent and storage in glass at $-80°$ C.; dark purple bars represent experiments conducted using media as the diluent and storage in polypropylene at +4° C.; pink bars represent experiments conducted using 1% sorbitol as the diluent and storage in polypropylene at +4° C.; light yellow bars represent experiments conducted using 10% PG as diluent and storage in polypropylene at +4° C.; turquoise blue bars represent experiments conducted using 25% PG as diluent and storage in polypropylene at +4° C.; dark green bars represent experiments conducted using 10% PG+0.2% TWEEN-80 as diluent and storage in polypropylene at +4° C.; light blue bars represent experiments conducted using 25% PG+0.2% TWEEN-80 as diluent and storage in polypropylene at +4° C.; green bars represent experiments conducted using 10% PG+0.5% TWEEN-80 as diluent and storage in polypropylene at +4° C.; dark blue bars represent experiments conducted using 25% PG+0.5% TWEEN-80 as diluent and storage in polypropylene at +4° C. The number "118" in the figure represents a specific experiment number.

The Effect of Added Excipients on the Stability of Recombinant AAV-Comparison of Storage in Glass and Polypropylene Vials The stability of the AAV vector was measured as described in Example 5. The formulations of excipients and results are given in FIG. 10. The data indicate that neither propylene glycol (PG) nor sorbitol alone protect against loss of activity of an rAAV sample stored in a glass vial. When PG and TWEEN were combined, loss of activity was minimized and, in fact, it appears that PG and TWEEN together may have a synergistic effect on activity.

EXAMPLE 8

The Effect of Added Excipients on the Stability of Recombinant AAV: The Effect of 5% Sorbitol These experiments were designed to study the effect of 5% sorbitol, in combination with various concentrations of TWEEN on the activity of rAAV.

Figure 11:
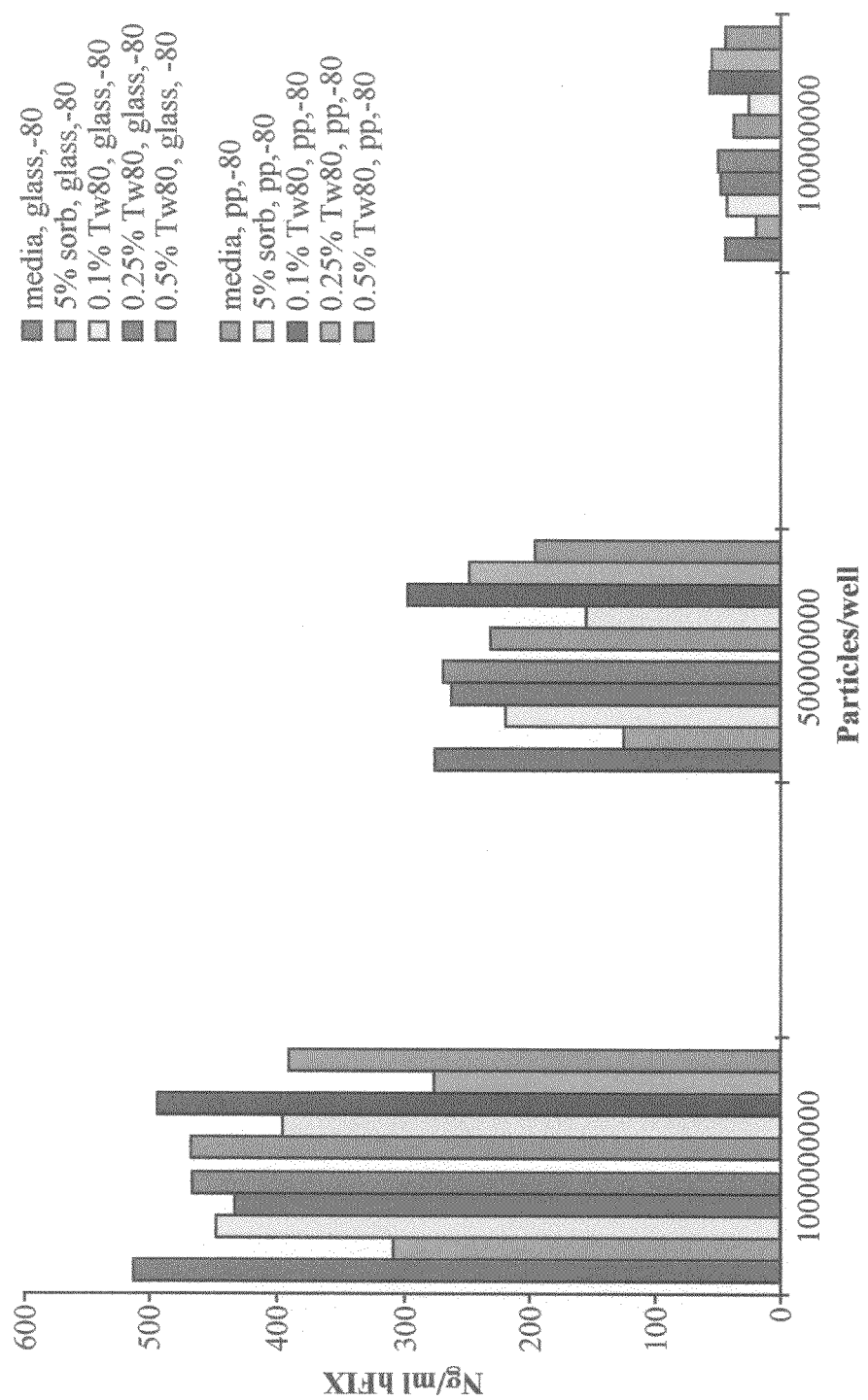
FIG. 11 depicts the results obtained in the experiment described in Example 8 to determine the effect of 5% sorbitol, alone and in combination with various excipients on the stability of recombinant AAV vectors after a freeze/thaw cycle Of samples stored in a glass vial or a polypropylene tube. Light blue bars represent experiments conducted using media as the diluent (without sorbitol) and storage in glass at –80° C.; pink bars represent experiments conducted using 5% sorbitol and storage in glass at –80° C.; yellow bars represent experiments conducted using 5% sorbitol+0.1% TWEEN-80 and storage in glass at –80° C.; green bars represent experiments conducted using 5% sorbitol+0.25% TWEEN-80 and storage in glass at –80° C.; light brown bars represent experiments conducted using 5% sorbitol+0.5% TWEEN-80 and storage in glass at –80° C.; turquoise blue bars represent experiments conducted using media as the diluent (without sorbitol) and storage in polypropylene at –80° C.; gray bats represent experiments conducted using 5% sorbitol and storage in polypropylene at –80° C.; blue bars represent experiments conducted using 5% sorbitol+0.1% TWEEN-80 and storage in polypropylene at =80° C.; lime green bars represent experiments conducted using 5% sorbitol+0.25% TWEEN-80 and storage in polypropylene at –80° C.; red bars represent experiments conducted using 5% sorbitol+0.5% TWEEN-80 and storage in polypropylene at –80° C.

The stability of the AAV vector after a freeze/thaw cycle was measured as described in Example 6 using 1×10⁸, 5×10⁸ or 1×10⁹ particles/well. Each sample was done in a glass vial or a polypropylene tube, and stored at −80° C. overnight. The formulations of excipients and results are given in FIG. 11.

A formulation containing 5% sorbitol provided a partial protective effect against loss of rAAV activity when the sample was stored in a glass vial. However, the addition of TWEEN provided a significantly greater protective effect.

Thus, formulations for enhancing the stability of recombinant AAV preparations are described. Although preferred embodiments of the subject invention have been described in some detail, it is understood that obvious variations can be made without departing from the spirit and the scope of the invention as defined by the appended claims.

We claim:
1. A pharmaceutical composition comprising recombinant adeno-associated virus (AAV) virions containing a heterologous nucleotide sequence, a detergent and at least one dihydric or polyhydric alcohol, wherein AAV virions in the composition are protected from loss of transduceability.

2. The pharmaceutical composition of claim 1, wherein the dihydric or polyhydric alcohol is one or more alcohols selected from the group consisting of polyethylene glycol, propylene glycol and sorbitol.

3. The pharmaceutical composition of claim 2, wherein the one or more alcohols is sorbitol and the sorbitol is present at a concentration of about 0.1 wt. % to about 10 wt. %.

4. The pharmaceutical composition of claim 3, wherein sorbitol is present at a concentration of about 1 wt. % to about 5 wt. %.

5. The pharmaceutical composition of claim 2, wherein the one or more alcohols is polyethylene glycol and the polyethylene glycol is present at a concentration of about 2 wt. % to about 40 wt. %.

6. The pharmaceutical composition of claim 5, wherein polyethylene glycol is present at a concentration of about 10 wt. % to about 25 wt. %.

7. The pharmaceutical composition of claim 2, wherein the one or more alcohols is propylene glycol and the propylene glycol is present at a concentration of about 2 wt. % to about 60 wt. %.

8. The pharmaceutical composition of claim 7, wherein propylene glycol is present at a concentration of about 5 wt. % to about 30 wt. %.

9. The pharmaceutical composition of claim 1, wherein the detergent is a nonionic detergent.

10. The pharmaceutical composition of claim 9, wherein the detergent is a sorbitan ester.

11. The pharmaceutical composition of claim 10, wherein the detergent is selected from the group consisting of polyoxyethylenesorbitan monolaurate (TWEEN-20), polyoxyethylenesorbitan monopalmitate (TWEEN-40), polyoxyethylenesorbitan monostearate (TWEEN-60), polyoxyethylenesorbitan tristearate (TWEEN-65), polyoxyethylenesorbitan monooleate (TWEEN-80) and polyoxyethylenesorbitan trioleate (TWEEN-85).

12. The pharmaceutical composition of claim 11, wherein the detergent is polyoxyethylenesorbitan monolaurate (TWEEN-20) present at a concentration of about 0.05 wt. % to about 5 wt. %.

13. The pharmaceutical composition of claim 11, wherein the detergent is polyoxyethylenesorbitan monooleate (TWEEN-80), present at a concentration of about 0.05 wt. % to about 5 wt. %.

14. A pharmaceutical composition comprising recombinant AAV virions containing a heterologous nucleotide sequence, said virions present in an amount sufficient to provide a therapeutic effect when given in one or more doses, sorbitol present at a concentration of about 1 wt. % to about 5 wt. % and a detergent present at a concentration of about 0.1 wt. % to about 1 wt. %, wherein the detergent is polyoxyethylenesorbitan monolaurate (TWEEN-20) or polyoxyethylenesorbitan monooleate (TWEEN-80), wherein AAV virions in the composition are protected from loss of transduceability.

15. A method for protecting a recombinant AAV virion containing a heterologous nucleotide sequence from loss of activity resulting from exposure of the virion to a cycle of freezing and thawing, said method comprising admixing the virion with a virion-stabilizing composition comprising sorbitol and a sorbitan ester selected from the group consisting of polyoxyethylenesorbitan monolaurate (TWEEN-20) and polyoxyethylenesorbitan monooleate (TWEEN-80).

16. A method for protecting a recombinant AAV virion containing a heterologous nucleotide sequence from loss of activity resulting from storage of the virion in a glass vessel comprising admixing the virion with a virion-stabilizing composition comprising sorbitol and a sorbitan ester selected from the group consisting of polyoxyethylenesorbitan monolaurate (TWEEN-20) and polyoxyethylenesorbitan monooleate (TWEEN-80).

* * * * *